(12) United States Patent
Cantwell et al.

(10) Patent No.: US 9,955,882 B2
(45) Date of Patent: May 1, 2018

(54) SYSTEM TO MONITOR NEURAL INTEGRITY

(71) Applicant: Medtronic Xomed, Inc., Jacksonville, FL (US)

(72) Inventors: Matthew L. Cantwell, Orange Park, FL (US); Bryan L. Courtney, Jacksonville, FL (US); David C. Hacker, Jacksonville, FL (US); Kevin L. McFarlin, St. Johns, FL (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 0 days. days.

(21) Appl. No.: 15/252,975

(22) Filed: Aug. 31, 2016

(65) Prior Publication Data

US 2018/0055393 A1    Mar. 1, 2018

(51) Int. Cl.
*A61B 5/04* (2006.01)
*A61B 5/00* (2006.01)

(52) U.S. Cl.
CPC ........ *A61B 5/04001* (2013.01); *A61B 5/6877* (2013.01); *A61B 2505/05* (2013.01)

(58) Field of Classification Search
None
See application file for complete search history.

(56) References Cited

U.S. PATENT DOCUMENTS

| | | | |
|---|---|---|---|
| 2003/0088185 A1 | 5/2003 | Prass | |
| 2008/0004673 A1 | 1/2008 | Rossing et al. | |
| 2008/0132983 A1* | 6/2008 | Cohen | A61N 1/0551 607/118 |
| 2010/0145221 A1 | 6/2010 | Brunnett et al. | |
| 2010/0145222 A1 | 6/2010 | Brunnett et al. | |
| 2011/0160827 A1 | 6/2011 | Bonde et al. | |
| 2011/0270357 A1 | 11/2011 | Torgerson et al. | |
| 2012/0016431 A1 | 1/2012 | Paul et al. | |
| 2013/0079745 A1* | 3/2013 | Thornton | A61N 1/36007 607/118 |
| 2013/0231726 A1* | 9/2013 | Johnson | A61N 1/0556 607/118 |
| 2013/0338749 A1* | 12/2013 | Brunnett | A61B 5/0488 607/116 |
| 2014/0094887 A1 | 4/2014 | True et al. | |
| 2014/0214129 A1* | 7/2014 | Waataja | A61N 1/36007 607/59 |
| 2014/0249601 A1 | 9/2014 | Bachinski et al. | |
| 2016/0038072 A1 | 2/2016 | Brown et al. | |
| 2016/0038073 A1 | 2/2016 | Brown et al. | |
| 2016/0038074 A1 | 2/2016 | Brown et al. | |

(Continued)

OTHER PUBLICATIONS

Medtronic, APS™ Electrode Stimulator Instructions for Use, 48 pages, 2010.

(Continued)

*Primary Examiner* — Ankit D Tejani
(74) *Attorney, Agent, or Firm* — Harness Dickey

(57) ABSTRACT

A stimulation electrode assembly configured to be positioned relative to a patient for an operative procedure is disclosed. The stimulation electrode may be a connection or self-contained component to contact a portion of a nerve. The stimulation electrode may provide or receive a signal to and/or from the nerve to assist in testing integrity of the nerve.

28 Claims, 8 Drawing Sheets

(56) References Cited

U.S. PATENT DOCUMENTS

| | | |
|---|---|---|
| 2016/0199659 A1 | 7/2016 | Jiang et al. |
| 2016/0287112 A1 | 10/2016 | McFarlin et al. |
| 2016/0287861 A1 | 10/2016 | McFarlin et al. |
| 2017/0007146 A1 | 1/2017 | Schulhauser et al. |
| 2017/0140121 A1 | 5/2017 | Schulhauser et al. |
| 2017/0140127 A1 | 5/2017 | Schulhauser et al. |

OTHER PUBLICATIONS

International Search Report and Written Opinion dated Dec. 4, 2017 in corresponding International Application No. PCT/US2017/049422.

* cited by examiner

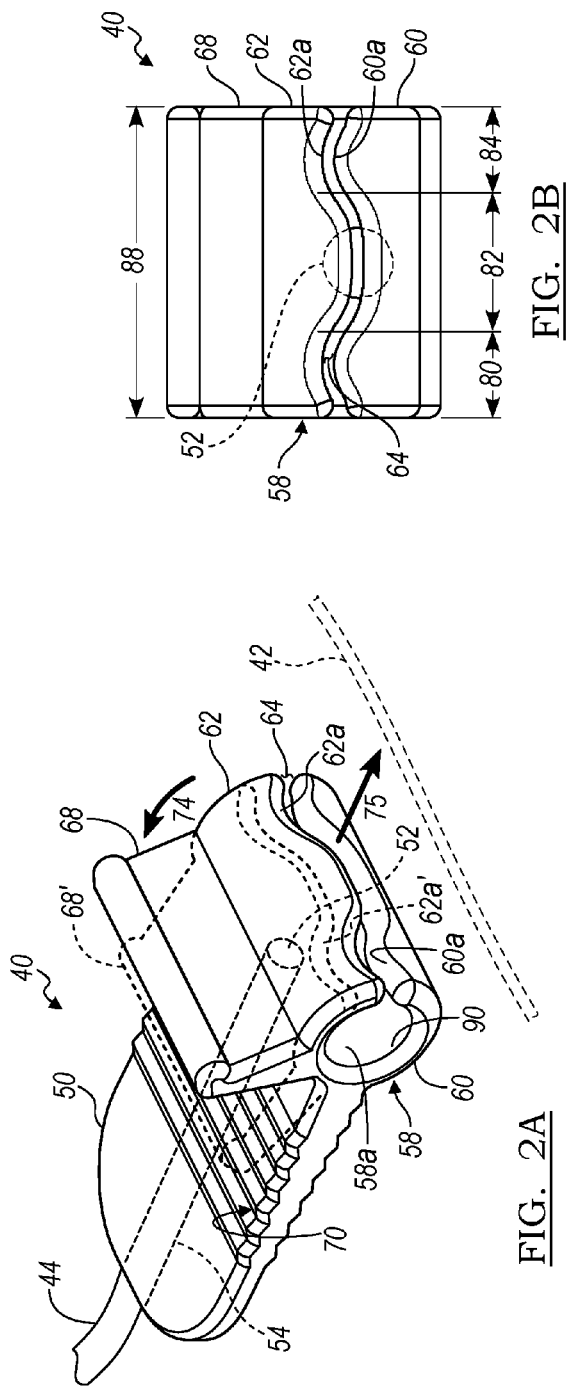
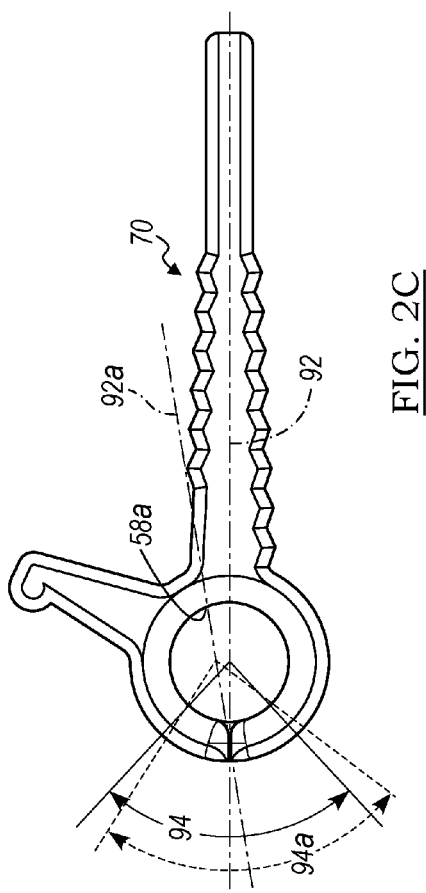
FIG. 2A
FIG. 2B
FIG. 2C

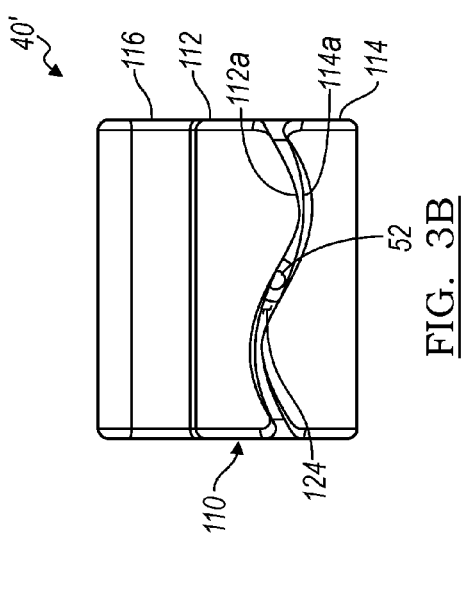
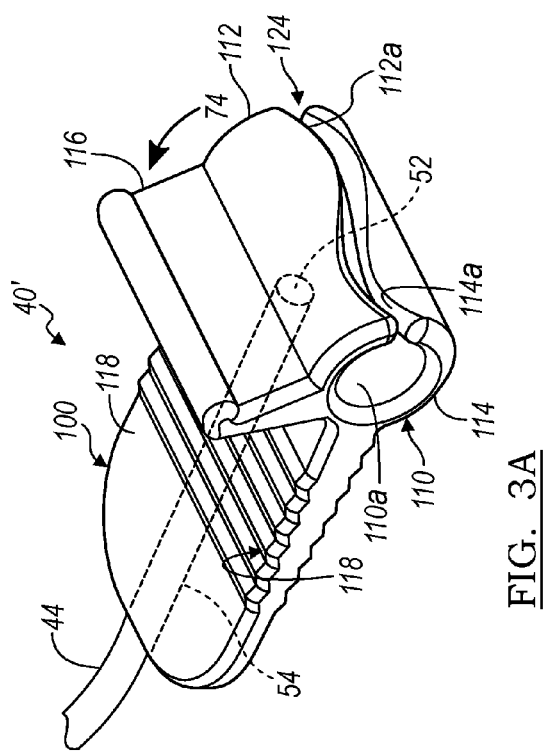
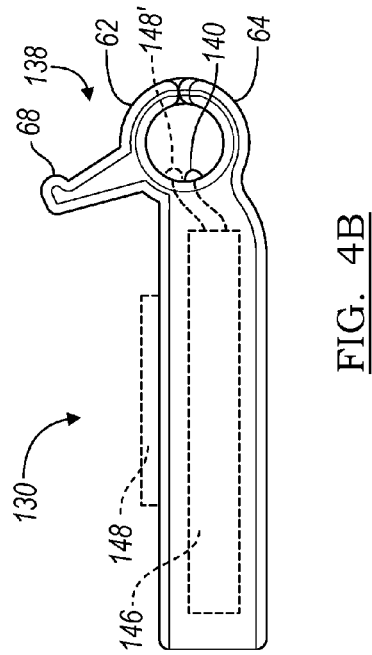
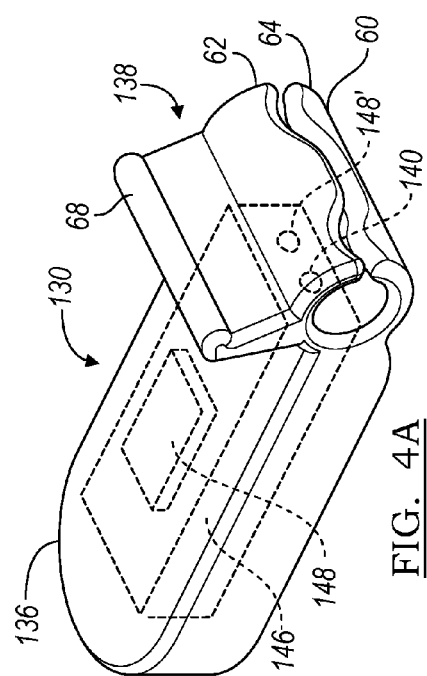
FIG. 3A
FIG. 3B
FIG. 4A
FIG. 4B

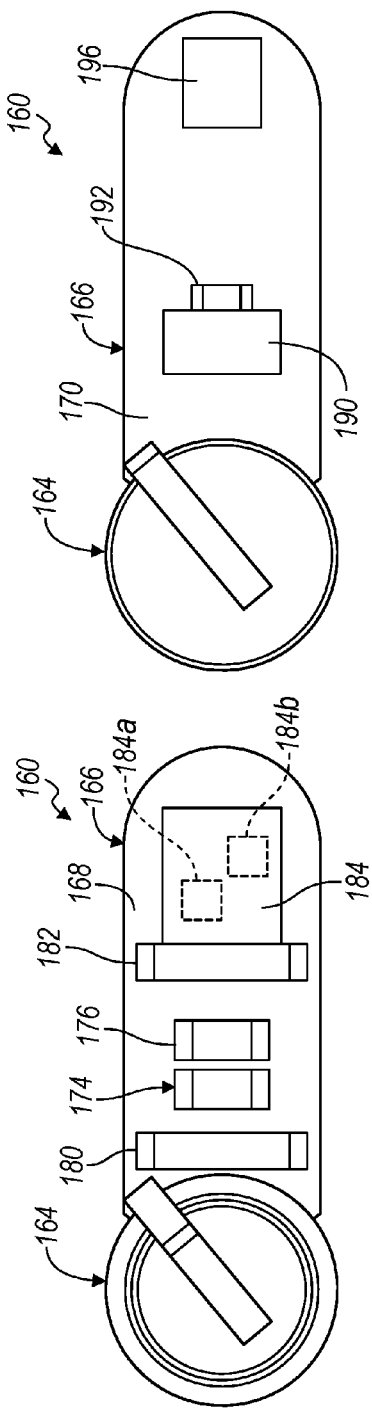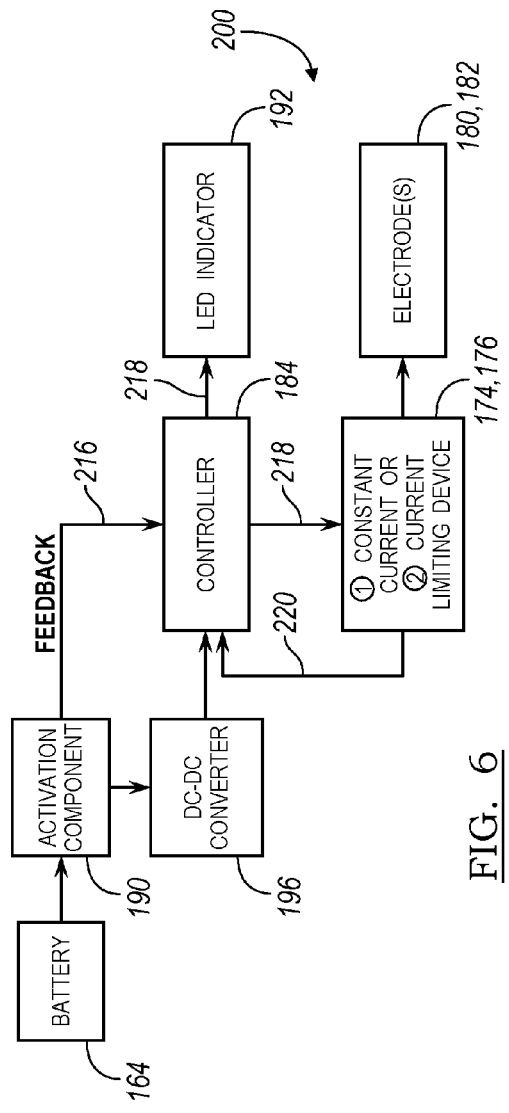

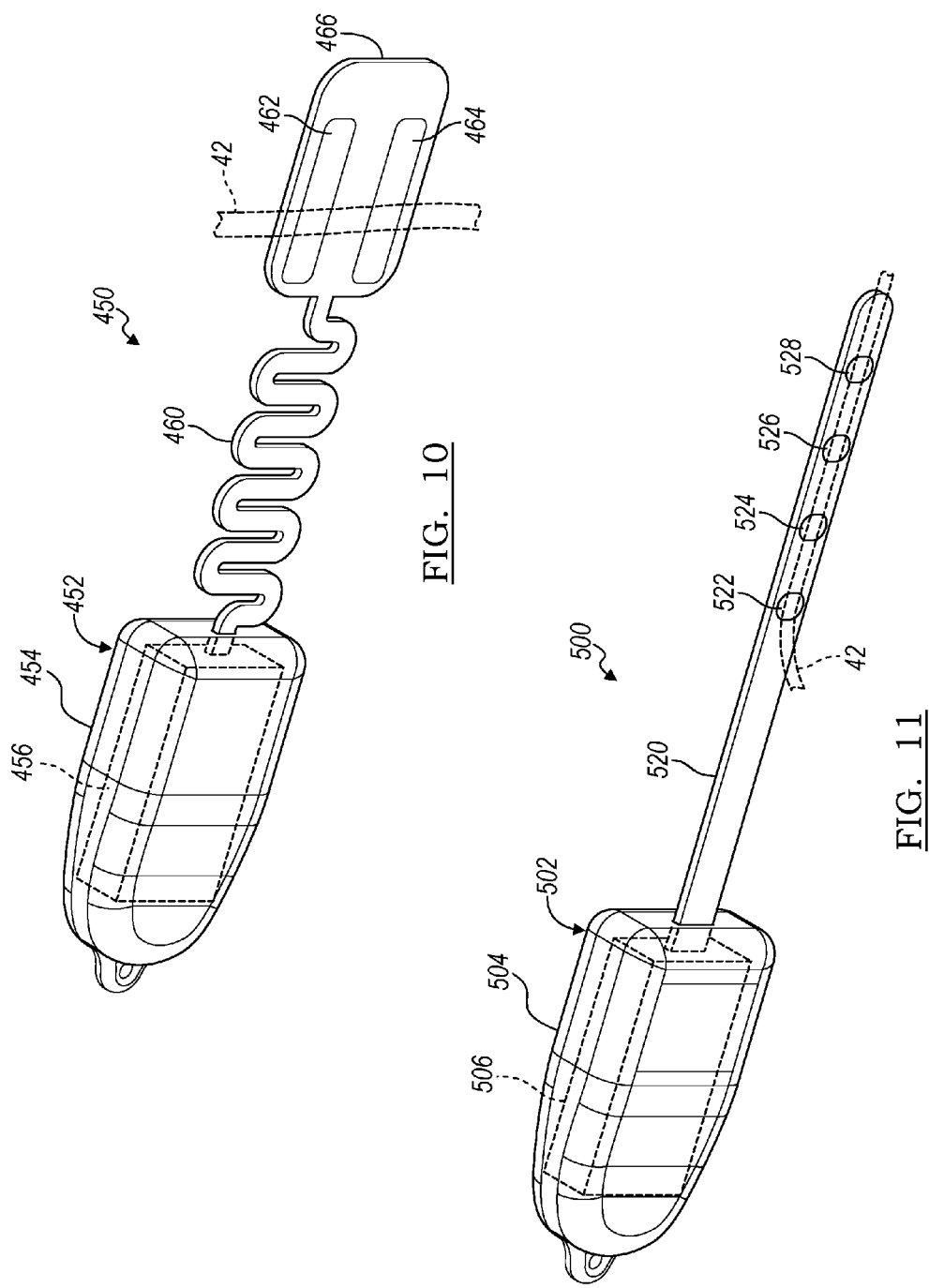

SYSTEM TO MONITOR NEURAL INTEGRITY

FIELD

The present disclosure relates to activity monitoring, and particularly to neural stimulation monitoring devices and methods.

BACKGROUND

This section provides background information related to the present disclosure which is not necessarily prior art.

During various procedures, such as various throat procedures or other procedures occurring near and/or adjacent to nerve fiber, a determination of nerve integrity or stimulation may be selected. Determining nerve integrity may include ensuring or monitoring stimulation activity along a nerve. This may include transmission of or receiving an induced signal on a nerve. In performing such integrity monitoring, an electrode or electrode containing element is connected to a nerve or nerve fiber to monitor or stimulate the nerve fiber. Monitoring of an induced signal at a single time or over a period of time can assist in determining integrity of a nerve. Various monitoring systems include the NIM-Response® 3.0 sold by Medtronic, Inc. having a place of business in Minneapolis, Minn. The monitor systems can include or be operated with an electrode including an APS® electrode that allows for automatic and periodic stimulation of a nerve that may be monitored by the system.

SUMMARY

This section provides a general summary of the disclosure, and is not a comprehensive disclosure of its full scope or all of its features.

A system to provide stimulation to selected nerve bundles or paths disclosed includes a selected cuff or selector for connected electrodes to nerve modules in a wired or wireless manner. Further, a wireless stimulator assembly can be positioned adjacent to or near a nerve for stimulating the nerve and/or detecting a stimulation of the nerve. The electrodes may include an active fixation that positively connect or surround at least a portion of the nerve bundle. In the alternative, the system may provide a contact electrode that contacts the nerve and is held in place by friction or compression of surrounding tissue.

The active or passive fixation systems may be provided in combination with either wired or wireless stimulation systems. The wireless electrode assemblies may also be referred to as leadless and do not require a physical connection to a monitoring system. The monitoring system may include a processor that can be a general purpose processor that is able to execute instructions stored in a memory. The memory may be a physical memory that is incorporated into the monitoring system or accessed via a network. The instructions are executed by the processor to analyze the received signals to assist in determining integrity of a nerve over time. The monitoring system may further include a display device or other output for a user to view the results of the monitoring.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2A is a perspective view of an electrode assembly, according to various embodiments;

FIG. 2B is a front view of the electrode assembly of FIG. 2A;

FIG. 2C is a side plan view of the electrode assembly of FIG. 2A;

FIG. 3A is a perspective view of an electrode assembly, according to various embodiments;

FIG. 3B is a front view of the electrode assembly of FIG. 3A;

FIG. 4A is a perspective view of an electrode assembly, according to various embodiments;

FIG. 4B is a side plan view of the electrode assembly of FIG. 4A;

FIG. 5A is a top plan view of an electronics package, according to various embodiments;

FIG. 5B is a bottom plan view of the electronics package of FIG. 5A;

FIG. 6 is a schematic of the electronics package and connections;

FIG. 10 is a perspective view of an electrode assembly, according to various embodiments;

FIG. 11 is a perspective view of an electrode assembly, according to various embodiments.

Corresponding reference numerals indicate corresponding parts throughout the several views of the drawings.

DETAILED DESCRIPTION

Example embodiments will now be described more fully with reference to the accompanying drawings.

Figure 1:
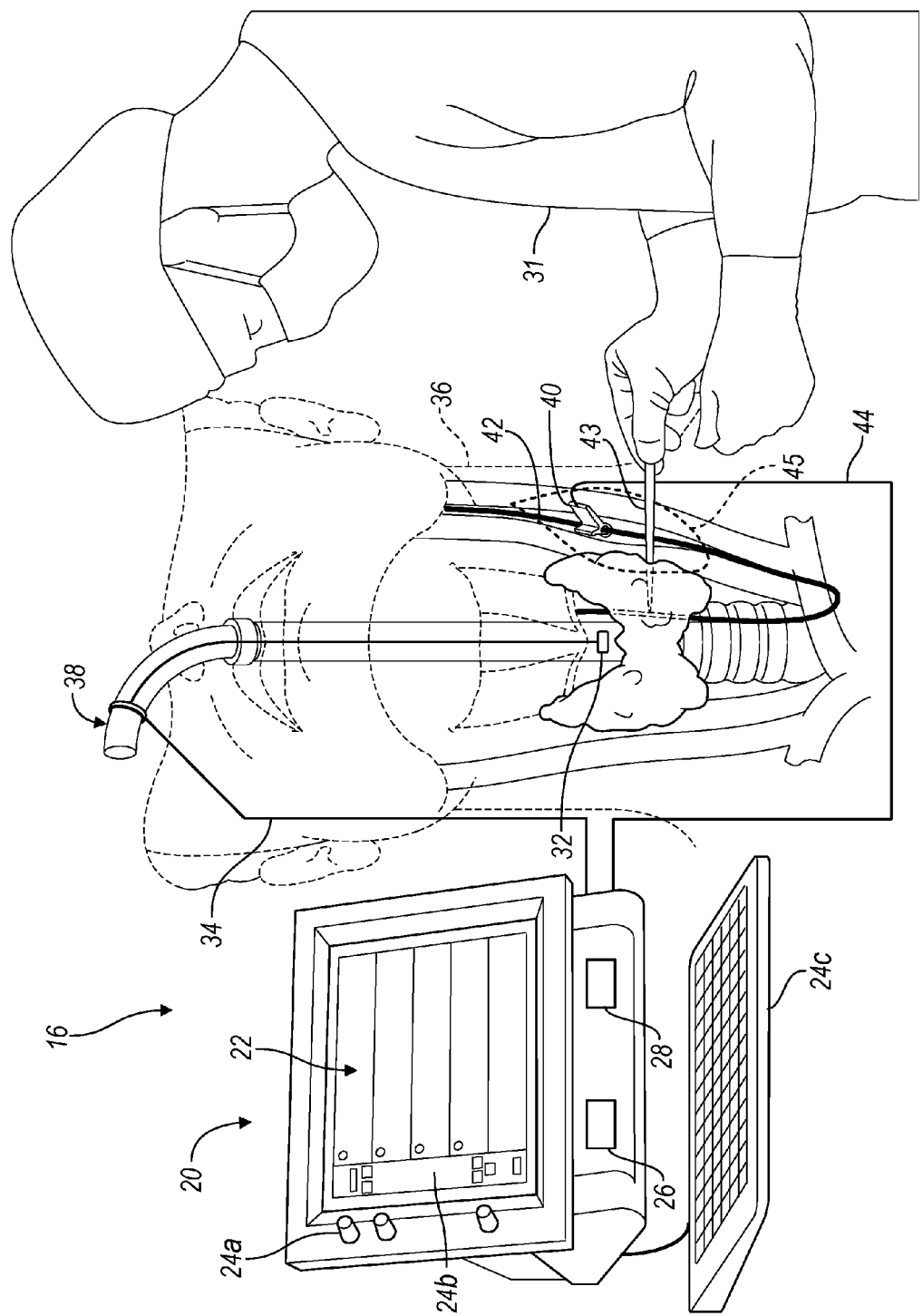
FIG. 1 is an environmental view of a monitoring system and an electrode assembly.

With initial reference to FIG. 1 a monitoring system 16, such as a NIM® nerve integrity monitoring system may include a monitor assembly 20 that has a display screen or device 22 and one or more input devices. The monitoring system may also include monitoring systems such as those disclosed in U.S. patent application Ser. No. 14/678,485, filed on Apr. 3, 2015 and U.S. patent application Ser. No. 14/678,452, filed on Apr. 3, 2015; both incorporated herein by reference. The input devise may include one or more systems or structures to input commands of information such as knobs 24a, a touch screen 24b, a keyboard 24c, or other appropriate input devices. Input devices may also include audio or other tactile input devices.

The monitor assembly 20 may further include a processor 26 and a memory 28. It is understood that the processor 26 may access the memory 28 to execute instructions stored thereon or access other data on the memory 28. The memory 28 may include a physical memory, such as a spinning hard disk drive, solid state memory, or other appropriate types of memory. Further, the memory 28 may not be incorporated into the monitor assembly 20, but may be accessed by processor 26, such as via communications network. The processor 26 may be a general purpose processor that is operable to execute instructions for generating a selected output, as discussed further herein. The processor 26 may further include onboard memory. Moreover, the processor 26 may include a specific purpose processor such as an application specific integrated circuit (ASIC). Accordingly, the processor 26 may execute instructions stored on memory 28, which may be a non-transitory memory, to provide an output for display on the display device 22. A user 31 may then view the display device 22 for selected purposes, as discussed further herein.

Connected with the monitor assembly 20, may be one or more stimulation or monitoring assemblies. For example, in various procedures such as a thyroidectomy or other thyroid surgeries, monitoring of a recurrent laryngeal nerve (RLN), a vagus nerve, or other appropriate nerve, in a patient 36 may be selected. Monitoring of the RLN may include a nerve monitoring esophageal tube 38, which may have one or more conductive electrodes 32 that are in contact with selected portions of the patient 36, such as a human patient. The electrode 32 can be connected to the monitor 20 via a connection 34. It is understood, however, that the connection to the monitor 20 may also be a wireless connection where the monitor 20 receives a wireless transmitted signal from the electrode 32.

In addition, other instruments may be connected to the monitor 20, such as electrode assemblies, including an electrode that may send or receive periodic stimulation pulses, including, according to various embodiments, connected cuff electrode assembly 40 as illustrated in FIG. 1 and further in FIGS. 2A-3B. The connected cuff electrode assembly may be connected with a physical connection, such as a wire 44 to the monitor 20. Other instruments may also be connected with the monitor 20 that may be used to send or receive stimulation signals to the patient to assist in determining whether nerve damage or other tissue damage has occurred or could occur. A scalpel 43 may be manipulated by the user 31, such as a human surgeon, need not be directly connected to the monitor 20. The monitor 20 may be provided to monitor signals through or from the electrode assemblies 32 and 40 without requiring interactive stimulation or monitoring through the scalpel or other selected instruments performing a procedure on the patient 36. As discussed herein, according to various embodiments, electrode assemblies may be connected to one or more nerves 42 to generate a stimulation to the nerve 42 at a selected rate. The rate may be selected to account for a refractory period of the nerve. Thus, a pause or period between stimulations may be selected to account for the refractory period.

The operation of the monitoring system and the use of the monitoring system 16 may be similar to the NIM® monitoring system sold by Medtronic, Inc., including the NIM-Response® 3.0 nerve monitoring system. In operation, the electrode assembly 40 may be connected with a nerve 42, as discussed further herein, and a signal may be transmitted along the connection 44 from the monitor system 20. The electrode 32 may be used to receive a signal that is transmitted through the nerve 42.

The electrode 40 may include a housing or case 50 that assists in maintaining contact of an electrode contact or button 52 in contact with the nerve 42. The communication line 44 may be electrically connected through the electrode button 52 via a connection portion 54, such as a wire or trace on a circuit board, through the casing 50.

With additional reference to FIG. 2A and FIG. 2B, the electrode housing 50 may be formed as a single piece or several pieces that are connected together. The electrode assembly 40, including the housing 50, may include a cuff portion 58 that is formed, for example, as a single unitary portion with the housing 50. In various embodiments, the housing 50 may be overmolded on the electrode button 52 and connector 54 in the shape and configuration of the housing 50 including the cuff portion 58. The single piece housing 50, however, may be molded of many materials that are molded into various positions of the housing 50. Alternatively, the housing 50 may be formed entirely of a single material and molded at a single time.

At least a portion of the cuff portion 58, such as a hinge region 58a, may be resiliently deformable. The hinge region 58a may be resiliently deformable based on the material formed in the hinge region 58a, geometry of the hinge region 58a (such as formed depressions or weak regions), or other appropriate design features. Accordingly, the cuff portion 58 may have a first portion 60 and a second portion 62. The second portion 62 may move relative to the first portion 60 to form an opening 64.

Movement of the second portion 62 may be actuated by pressing an integrated or unitarily formed lever arm 68 towards a surface 70 of the housing 50. For example, the user 31 may hold the housing assembly 50 in a hand and press on the lever arm 68 with a thumb or digit to press the lever arm 68 towards the surface 70. Alternatively, the user 31 may grasp the electrode assembly 40 with an instrument, such as forceps or tweezers, to move the lever arm 68. This will cause the lever arm 68 and the second portion 62 to generally move in the direction of arrow 74 causing the opening 64.

The opening 64 may allow the housing assembly 50 to be positioned over or around the nerve 42. Releasing the lever arm 68 will allow the resiliently deformable portion to relax to the closed position and close the opening 64 between the first and second portions 60, 62. In the closed position, the first member 60 and the second member 62 may contact one another at respective terminal edges 60a and 62a around the nerve 42. Once closed, the electrode button 52 may contact or be in an electrical contact with the nerve 42 to either provide or receive a stimulation signal.

The opening 64 may include a plurality of regions, such as a first region 80, a second region 82, and a third region 84. The three regions of the opening 64 may be distinguished or separated due to a geometry of the opening 64 across a width 88 of the electrode assembly 40. For example, the first region 80 may have an arc that has a center near the first portion with an arc arcing towards the second portion 62. The third section 84 of the opening 64 may include a singular geometry as the first section 80. The second region 82 may include a generally inverse geometry where an arc is formed that extends towards the first section 60 or into the first section 60 and having a center closer to the second section 62. The second region 82 may also include a flat region rather than having a continuous curve. The opening 64, a configuration of the opening 64, and a position of the opening 64, may include an appropriate geometry to assist in engaging or operating the cuff 58 of the electrode 40 to engage the nerve. As discussed herein, a non-linear opening may assist in resisting radial removal from the nerve 42. The position of the opening 64 may assist in minimal movement to open the opening to engage the nerve.

As illustrated in FIG. 2A, the cuff 58 may include a generally annular configuration including an internal wall 90 that extends generally in a circle around a long axis of the cuff 58. The first portion 60 may extend a greater distance from the hinge region 58a towards the opening 64 then the second portion 62 extends from the end region 58a to the opening 64. Therefore, the opening 64 may be formed generally in line or in the same plane with the surface 70.

With additional reference to FIG. 2C, the opening 64, even though it includes a shape or geometry, may also be generally formed or positioned within an opening region 94 of the cuff 58. The opening region 94 may be defined as a region that is generally within 5° to 20°, including about 5° to 10°, from a plane 92 defined by or near the surface 70. An opening region 94a may also be defined as generally within 5° to 20°, including about 5° to 10°, from a plane 92a defined through the hinge area 58a and the opening 64 or where the edges 60a and 62a meet when closed. The opening region 94, 94a may define or limit a region where the edges 60a, 60a meet when closed. The opening region 94, 94a may also or alternatively define an extent of maximum openness of the opening 64. It is understood, however, that the opening need not be as great as the opening region 94, 94a, but may be formed within the opening region 94, 94a.

In providing the opening region 94, 94a, the user 31 need not open or move the lever 68 a great distance to opening the opening 64 great enough to receive or pass over the nerve 42. Further, the configuration of the edges 60a, 62a to form the opening 64 allow for the electrode assembly to be placed generally along a straight line over the nerve 42 to engage the nerve 42. Also, by forming the opening 64 to have an extent no greater than the opening region 94, 94a the electrode assembly 40 may be moved over the nerve 42 in a substantially straight line. The electrode assembly 40, therefore, need not be twisted to be placed over the nerve 42.

As illustrated in phantom in FIG. 2A the lever 68 may be moved to an open position 68', by the user 31. By moving the lever to the open position 68', at least the cuff portion 602 may move to the open position shown in phantom at 60'; thus, the opening 64 may be made. Once the user 31 has formed the opening 64, the electrode assembly 40 may be moved in a substantially straight line or along an axis 75 to engage the nerve 42 (illustrated in phantom in FIG. 2A). Thus, the electrode assembly 40 may be placed on the nerve 42 without twisting the electrode assembly 40. Further, the opening 64 may be formed that is large enough to be moved over at least a portion of the nerve to allow the electrode assembly to engage the nerve 42 by moving the lever 68 and forming the opening 64 in the opening region 94, 94a. As discussed above, it may be selected to form only the opening in the opening region 94, 94a and the electrode assembly 40 may engage the nerve 42.

The position of the opening in the opening region 94, 94a and the shape of the edges 60a, 62a assist in ensuring that the electrode assembly 40 may be placed over and/or to engage the nerve without twisting the electrode assembly 40 around the axis formed by line/arrow 75. The electrode assembly 40 may be moved in a generally straight line to engage the nerve 42. Further, the amount of movement of the lever 68 and the cuff portion 60 may be about 5 to 40 degrees to form the opening to a large enough area to move over the nerve 42. The user 31, therefore, may obtain access to the nerve 42 and efficiently and effectively place the electrode assembly 40 on the nerve 42.

With reference to FIGS. 3A and 3B, an electrode assembly 40' may include a casing 100 that is similar to the casing 50 as described above. The electrode 40' illustrated in FIGS. 3A and 3B may include portions that are substantially similar to portions illustrated in FIGS. 2A-2C and those portions will not be re-described in detail here. Nevertheless, the electrode 40' may include a casing 100 may be formed as one or many pieces to include a cuff region 110. The cuff region 110 can also include a hinge region 110a that can be formed similar to the hinge region 58a of the cuff 58. The cuff 110 also operates in a manner similar to the cuff 58 and includes a first portion 112 and a second portion 114 with a lever arm or portion 116. The cuff 110 may be opened by moving the lever 116 towards an upper surface 118 of the casing 100. Exposed within the cuff 110 may be the electrode button or contact 52 which may be connected with the connector 44 through the internal connector 54.

The cuff 110 may be opened by moving the lever 116 to expose or form an opening 124 between an edge 112a of the first portion 112 and an edge 114a of the second portion 114. Movement of the lever arm 116 generally in the direction of arrow 74 causes the opening 124 to be formed. The edges 112a and 114a may include a selected shape, such as one that is that is generally similar to a sinusoidal wave. Again, at the opening 124 may generally be formed in an opening region similar to the opening region 94, 94a as discussed above. As discussed above, the opening 124 being within the opening region 94, 94a may allow for efficient placement of the electrode assembly 40' on the nerve 42 by the user 31. The electrode assembly 40' may be placed on the nerve generally in a straight line and without twisting of the electrode assembly 40'

As discussed in relation to the electrode assembly 40, the electrode assembly 40' may be moved generally along a line or axis 75 to engage the nerve 42. The electrode assembly 40' need not or may need not be twisted around an axis of the line 75 to engage the nerve 42. Again, the lever 116 and the cuff portion 112 may be moved, such as only moved, about 5 to about 40 degrees to form the opening 124 to allow the electrode assembly 40' to engage the nerve.

Both of the electrodes 40 and 40' may be connected via the connector 44 directly with the monitor system 20. Accordingly, a signal may be transmitted along the connector 44 to the monitor system 20 for monitoring of a transmission along the nerve 42. The electrodes 40, 40', however, can include the openings 64 and 124, respectively, to assist in positioning the electrodes 40, 40' on the nerve 42. The respective cuffs 58, 110 may require a substantially complete dissection around the nerve 42 to allow connection of the electrodes 40, 40' to the nerve 42.

The openings 64, 124 in the opening region 94, however, may allow the user 31 ease of placement of the electrodes 40, 40' on the nerve 42. As the electrode assemblies 40, 40' may be inserted in a substantially straight line with no twisting to place the cuff 58, 110 around the nerve 42, securing the electrode assemblies 40, 40' to the nerve 42 is efficient. The user 31 may remove enough tissue to expose the surface of the nerve 42 and then form the opening 64 or 124 of the respective electrode assemblies 40, 40' and push the electrode onto the nerve 42 and then release the respective levers 68, 116 to cause the cuffs 58, 110 to close around the nerve 42. As the respective openings 64, 124 are formed within the opening region 94 placement around the nerve 42 may be efficient.

Electrode assemblies, according to various embodiments, discussed further herein, may be provided that are not physically connected with the monitor 20, such as with the wire connection 44. The electrode assemblies, as discussed in various embodiments herein, may be leadless. Further, the leadless electrode assemblies need not have a direct communication with the monitor system 20. For example, the controller 20 need not directly or control the leadless electrode assemblies. As discussed herein, the leadless electrode assemblies may include a controller and/or power source to automatically (i.e. upon activation) provide a stimulation pulse to the nerve 42. The stimulation pulse may be detected by the monitor 20 to ensure that the nerve 42 is still intact. Thus, direct communication or control from the monitor 20 may not be present with the leadless electrode assemblies.

According to various embodiments, as illustrated in FIGS. 4A and 4B, a stimulator or electrode assembly 130 is illustrated. The electrode assembly 130 may be a leadless electrode assembly that is generally self-contained and self-powered, as discussed further herein. The electrode assembly 130 includes the system, as discussed herein, to stimulate and/or receive stimulus through a nervous system of a subject, such as the patient 36. The stimulator assembly 130 may provide a stimulation signal through the nerve 42, or other selected nerve, according to a predetermined frequency or program (e.g. such as a program of instructions stored with a controller in the electrode assembly 130). In other words, the electrode assembly 130 may provide an electrical stimulus to the nerve 42 according to a selected frequency, as discussed herein. The electrode assembly 130 may be self-contained and can include instructions that are executed by a selected processor (such that the electrode assembly 130 may operate automatically), as discussed further herein, to stimulate or provide a signal to the nerve 42. The electrode assembly 130 may be operated in a manner similar to the APS® electrode provided with the NIM® monitoring system sold by Medtronic, Inc.

Generally, the electrode assembly 130 can include a casing 136 that may be formed to include or connected to a cuff assembly 138 similar to the cuff assemblies discussed above, including the cuff assembly 58. Accordingly, the cuff assembly 138 may include a lever 68, a first cuff portion 60 and a second cuff portion 62. The two cuff portions 60, 62 can be moved to form the opening 64. The electrode assembly 130 can further include an electrode button or contact 140 that is in communication with an internal electronic components package 146 formed within the casing 136 of the electrode assembly 130.

As discussed above, the cuff assembly 138 may be manipulated to allow the cuff portion to be opened by moving the first or second cuff portion 60, 62 and positioning it over the nerve 42 to allow the nerve to be in contact with the electrode contact 140. A stimulation signal can then be provided through the contact electrode 140 and through the nerve 42. The contact electrode 140 may operate as a cathode and may operate similar to the wired electrodes 40, 40'. The conductive portion, such as the electrode 32, on the tube 30 may operate to receive the signal to confirm connection or integrity of the nerve 42 in the patient during a procedure.

One skilled in the art will understand, however, that a second contact electrode 148 (shown in phantom) may be formed on the case 136 and also be provided in contact with tissue of the subject 36. The second electrode 148 may operate as an anode for the electronic transmission system. A signal, if two electrodes 140, 148 are provided on the electrode assembly 130 can be received in the monitor system 20 by decoding or identifying the signal from the electrode assembly 130. By identifying the signal through the nerve 42, the monitor system 20 may be used to determine the integrity of the nerve 42 or other associated nerves.

The stimulation component or electronics package 146 can include an electronics assembly 160 illustrated schematically in FIGS. 5A and 5B. The electronics assembly 160 may operate with a self-contained power source 164, such as a battery. The electronics assembly 160 may be formed on a printed circuit board (PCB) 166 that may include a first side 168 and a second side 170. Components may be interconnected via the printed circuit board 166 with traces formed on the printed circuit board 166 and/or vias through the PCB 166. The electronics assembly is provided to operate the leadless electrode to provide stimulation pules, as discussed herein.

The electronics assembly 160 can include various electronic components, including capacitors, resisters, amplifiers, and other selected electronic components as generally understood by one skilled in the art. The various electronic components may include those discussed herein and as illustrated in FIG. 5A. It is understood that any appropriate number of electronic components may be provided and may be depended upon specific power output requirements, voltage requirements, low power requirements, and other selected features.

The electronics assembly 160, however, may include main components such as a first electrode 180. It is understood that more than one electrode may be provided, such as a second electrode 182. Further, the electronics assembly 160 may include a controller 184. The controller 184 may include a micro-controller that includes internal physical memory 184b that may store firmware including instructions to be executed by a controller processor 184a. The controller 184 may include a general purpose processor as the processor 184a that executes the instructions stored on the physical memory 184b and/or may be a specific processor formed to execute predetermined instructions. The controller 184, therefore, may include the controller processor 184a and internal memory 184b. The internal memory 184b may store the instructions for operation of the electronics assembly 160.

According to various embodiments, the electronics assembly 160 may include further components for operation of the electrode 130. For example, an activation component 190 may be provided, such as an optical sensor that may sense light at a selected wavelength, such as visible light, infra-red light, etc. The optical sensor may be used as a switch to activate the electrode assembly 130. A visual indicator 192, such as an LED indicator, may also be provided. Further, the electronics assembly 160 may include a DC-to-DC convertor 196. The DC-to-DC converter 196 may provide a selected voltage from the power source 164 to other components, such as the controller 184 and the electrodes 180, 182. The DC-to-DC converter 196 may be a step-up converter to step-up a voltage from the power source to an operating voltage for components of the electronics assembly 160. The electrodes 180, 182 may be to contact or be connected to contacts to contact the nerve 42.

The electronics assembly 160 may provide stimulation to a selected portion of the patient 36, as discussed above, through one or more electrode contacts in electrode 130. The electronics assembly 160 including the first and second electrodes 180, 182 may be directly exposed through the casing 136 of the electrode 130 and/or may be electrically connected to the electrode contacts 148 and 140. Nevertheless, the operation of the electronics assembly 160 may be provided via the operation of the components provided with the electronics assembly 160 according to an operational flow as schematically illustrated in FIG. 6. Further, various components may be provided on the stimulation component for various purposes, such as selecting a size of the electronics assembly 160 for inclusion in the electrode 130 or electrodes as discussed further herein. For example, step-up converters may be provided on the electronics assembly 160 to allow for operation of the electronics assembly 160 with voltage other than that provided directly by the single power supply, such as the battery 164. Moreover, the electronics assembly 160 may be activated according to various techniques, such as those discussed further herein.

In operation, with reference to FIG. 6, the electronics assembly 160 may operate in a substantially automatic manner. It is understood that various portions may be operated with manual intervention or manual activation, but the electronics assembly 160 may operate in a substantially automatic manner, as discussed herein, according to the flowchart 200 for most of the useful life (e.g. stimulation of the nerve 42) of the electronics assembly 160. In particular, as illustrated in the flowchart 200, a constant power may be supplied at a low current to an activation component 190. The activation component can include any appropriate component, such as the optical sensor 190. Other activation components 190 will be discussed further herein and all may operate to activate the electronics assembly 160 per the scheme illustrated in the flowchart 200.

Upon activation of the electronics assembly 160, the DC-to-DC convertor 196 may increase or step-up a base voltage of the power supply, such as the battery 164, to a selected voltage. The battery 164 may have a base voltage of about 1.5 volts. The DC-to-DC convertor 196 may increase or step up the voltage from the battery voltage to an operating voltage that is about 4 volts to about 5 volts, including an operating voltage nominally of about 4 volts. The controller 184 (which may include a micro-controller) may then operate on the increased voltage from the DC-to-DC convertor 196. The controller 184 or other appropriate dedicated activation circuitry may also receive a signal directly from the activation component 190 via a signal line 216 (e.g., via a trace on the PCB 166). The signal from the activation component 190 may operate to signal the controller 184 or other appropriate dedicated activation circuitry to turn ON. Turning on may include initiating operation of the processor 184a. Initiation of operation of the controller 184 may also include the activation signal 216 or directly due to a voltage from the DC-to-DC convertor 196.

Once the controller 184 is activated, the controller 184 may send a signal or set a signal 218 to the LED indicator 192. The LED indicator may provide a visual indication that the electronics assembly 160 is activated so that an operator, such as the user 31, is advised that the electronics assembly 160 is active. Activation of the electronics assembly 160 may include initiating transmitting current to or providing a voltage relative to a ground from the electrodes 180, 182. The indication of activation, therefore, allows the user 31 to understand that current is being drawn from the battery and the usable life of the battery 164 is being reduced.

The LED indicator 192 may be in the appropriate LED indicator and may be a steady visual indication, a blinking visual indication, or other appropriate indication. The optical sensor 190 and the LED component 192, as illustrated in FIG. 5B, may be provided in a portion of the casing, such as the casing 130, that is substantially transparent. The transparent portion may be transparent to allow a light source, such as ambient light or light from a flashlight, to reach the optical sensor 190 to activate the electronics assembly 160 and transparent to allow the emission of light from the LED indicator 192 for viewing by the user 31.

The controller 184 may be programmed, such as via instructions stored in the memory 184b, to provide a current to the electrodes 180, 182 via one or more electronic components. As discussed above, the electronics assembly 160 can include the main components discussed above and other operational components 174, 176. The operation components 174, 176 may be provided together or individually in the electronics assembly 160. For example, a constant current may be provided to the electrodes 180, 182 via an operational (OP) amplifier or active component that receives feedback to provide constant current to the electrodes 180, 182. The constant current component may provide to the electrodes 180, 182 the current directly provided through the controller or as controlled or selected from the DC-to-DC convertor 196. A feedback loop or signal 220 may also be provided to the controller 184 from the operation components 174, 176 regarding voltage at or signal to the electrodes 180, 182 and/or the patient 36.

In an alternative and/or concurrent operation, the operation of operation components 174, 176 may be a current limiting device. The current limiting device may limit the current of the signal 218 that is transmitted to the electrodes 180, 182. The current limiting device may be a resistor installed on the circuit board 166 of the electronics assembly 160. The resistor may be provided to simply reduce a current transmitted from the controller 184 to the electrodes 180, 182 as selected for operation of the electronics assembly 160.

Further, the controller 184 may generate a voltage directly through the signal 218 to the constant current component and/or the current limiting device 174, 176 for operation of the electronics assembly 160 at a selected stimulation voltage and/or current. Alternatively, the controller 184 may send an enabling signal as the signal 218 to the operation components 174, 176 to provide the stimulation through the electrodes 180, 182, such as with a current directly from the DC-to-DC converter 196. Therefore, the controller 184 may operate as the voltage providing component or may simply operate as an enabling controller to operate or transmit a signal through electrodes 180, 182.

Further, controller 184 may operate the signal 218 in a pulsing manner such that pulses are directed to the electrodes 180, 182 at a selected frequency. A frequency may be selected by the user 31 and/or manufacturer for operation with the monitor 20.

Further, the controller 184 may be operated in a selected manner to alternate or selectively power the electrodes 180, 182 individually and/or on an alternating basis. Accordingly, the electrode 180 may be operated at a time $T_0$ and the second electrode 182 may be operated at a time $T_1$. The time difference or time differential between $T_0$ and $T_1$ may be a selected delay such as about 10 milliseconds to about 500 milliseconds. The first electrode 180 may then be operated at a time $T_2$, following $T_1$, at a selected delay after operation of the second electrode 182 and the sequence may continue to alternate between the electrodes 180, 182. It is further understood that a selected plurality of electrodes, such as more than two electrodes, may be provided with the electronics assembly 160, as discussed further herein, to offer operation of the electronics assembly 160 with the monitor 20.

In various embodiments, the electrodes 180, 182 may also or alternatively be operated simultaneously with opposing electrical polarity (e.g. electrode 180 as a cathode and electrode 182 as an anode) at time $T_0$ for a period of time such as about 10 milliseconds to about 500 milliseconds. An inactive resting period (i.e. no electrical signal is provided to the electrodes 180, 182) of time, such as about 10 milliseconds to about 500 milliseconds, may elapse between $T_0$ and $T_1$. Electrodes 180, 182 may then also be operated at time $T_1$ simultaneously in reverse polarity with respect operation at time $T_0$ with opposing electrical polarity (e.g. electrode 180 as an anode and electrode 182 as a cathode) for a period of time such as about 10 milliseconds to about 500 milliseconds.

Further, controller 184 may operate the indicator 192 by a signal through connection 218 to provide various information to the user 31. For example, a fixed or selected blinking rate may be provided to indicate to the user 31 that the electronics assembly 160 has been activated and is operating in a nominal manner. A second blink rate, an alternate indicated color, or fixed indication signal may indicate different states of the electronics assembly 160, such as a low battery or end of life indication. Therefore, it is understood that the controller 184 may be operated to provide a signal through the electrodes 180, 182 and to provide a signal to the user 31, such as operating the LED indicator 192, in various manners.

Figure 7:
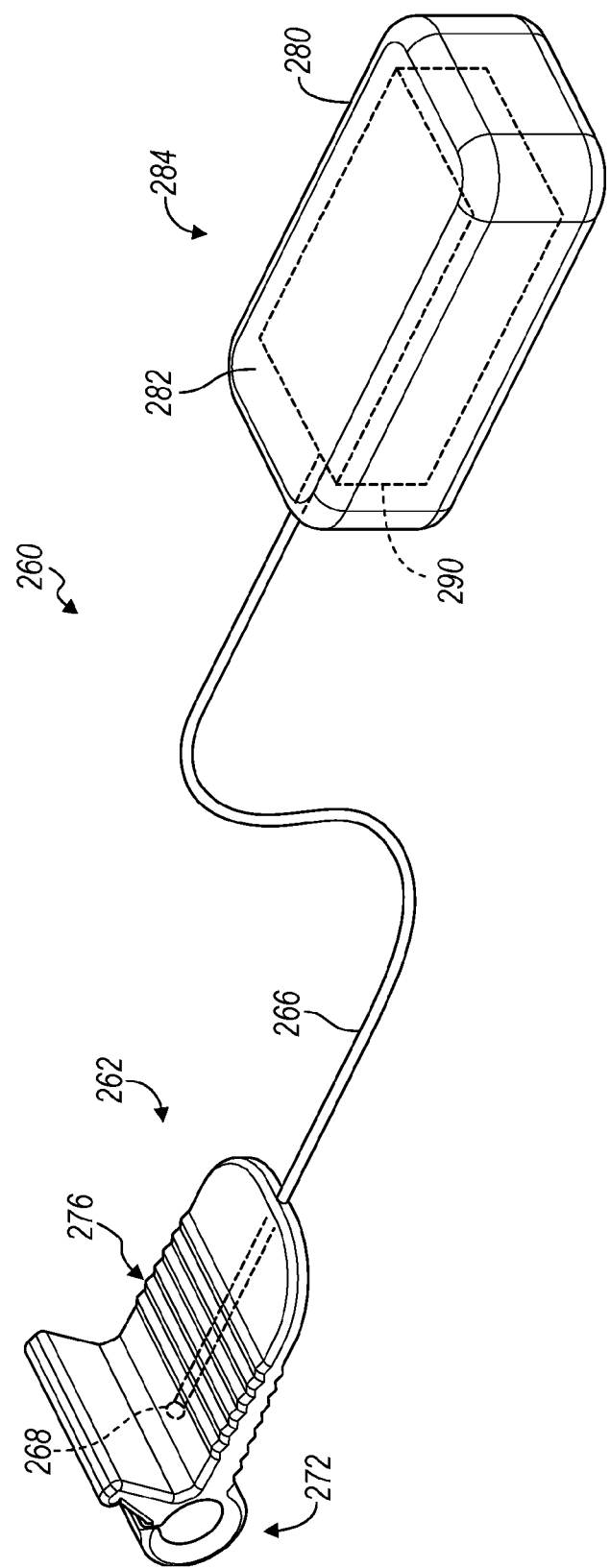
FIG. 7 is a perspective view of an electrode assembly, according to various embodiments.

Turning reference to FIG. 7, an electrode assembly 260 is illustrated. The electrode assembly 260 may be a leadless electrode assembly and includes a cuff electrode assembly 262 and a body anode assembly 284. The cuff cathode assembly 262 may be similar to the electrodes 40, 40' discussed above. In particular, a wired connection 266 may be formed between the cuff assembly 262 and the body component 284. An electrode contact button or contact 268 may be formed to contact the nerve 42 when a cuff portion 272 is operated, such as in a manner similar to the cuff portions discussed above, to contact with a nerve. The electrode contact 268 may be formed within a body 276 such as by overmolding the connection 266 and/or the electrode contact 268 and may also form the cuff portion 272.

The body anode portion 284 may include a case 280 that may be formed of a selected material, such as a metal conducting material. If case 280 is conductive, the entire case 280 may form an electrode. It is further understood, however, that only a selected portion, such as an anode surface 282, may be formed of a conductive material to form an electrode for contact with the anatomy of the patient 36. The body 284 may house an electronic portion 290, which may include all or part of the electronics assembly 160. As discussed above, the electrodes 180, 182 may be interconnected with contact portions such as the electrode contact 268 and the casing 280, 282 to provide conductive contact with portions of the patient 36. Therefore, the electronics assembly 160 may be provided as the electronic component 290 and the stimulator electrode 260 may be operated as discussed above according to the process discussed in relation to flowchart 200.

The stimulation electrode 260 may be positioned in the patient by providing the cuff portion 272 around the nerve 42. The body assembly 284 may be positioned in a selected location near, but away from, the nerve 42. The operation of the stimulation electrode 260, however, may operate in a manner as discussed above to stimulate the nerve to allow the monitor 20 to monitor nerve integrity during an operative procedure.

The stimulation electrode 260 may be operated in a monophasic or biphasic configuration given the two electrodes spaced apart, in a manner similar to the stimulation electrode 130 discussed above. The monophasic stimulation may include activating only one electrode or all of the electrodes contacting the patient, such as the electrode contact 268 and the electrode contact 282, at a fixed electrical polarity (e.g. during activation electrode contact 268 may always be the cathode and electrode contact 282 may always be the anode). The biphasic stimulation may include stimulating the patient through two of the electrodes, such as the electrode contact 268 and the electrode contact 282, in an electrically alternating polarity manner. The biphasic stimulation may allow for enhanced nerve response and improved insensitivity to the spatial placement of the electrodes. Further, the biphasic stimulation may allow for varying voltage stimulations at different points along the nerve 42.

Figure 8:
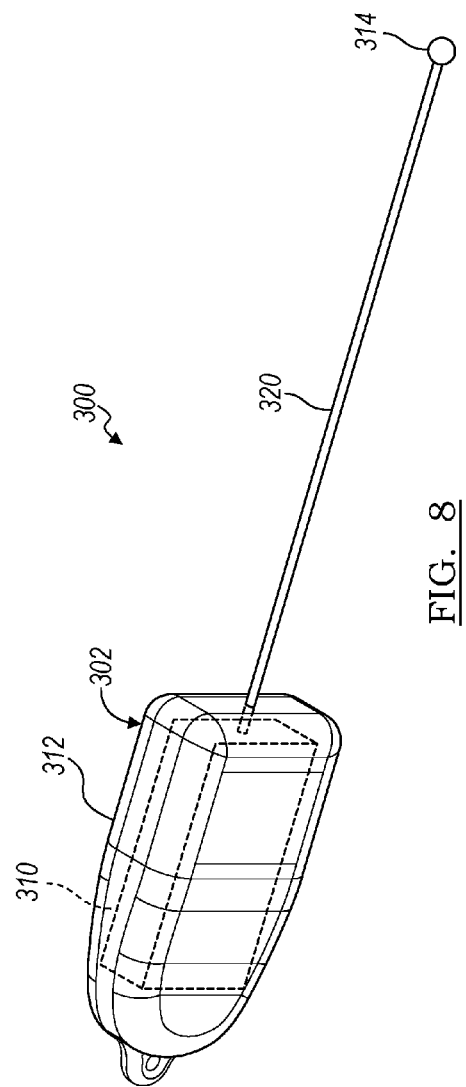
FIG. 8 is a perspective view of an electrode assembly, according to various embodiments.

Turning reference to FIG. 8, a stimulation electrode 300 is illustrated. The stimulation electrode 300 may be a leadless electrode assembly and may include a body portion 302 that surrounds an electronic package 310 that may include most of the components similar to the electronics assembly 160, as discussed above. As discussed above, the electronics assembly 160 may include two electrodes 180, 182 that may directly contact or may be connected with electrode contacts to directly contact the patient 36. The stimulation electrode 300, therefore, may include a surface electrode or electrode contact 312 that may operate as an anode and a distal or spaced apart cathode electrode contact 314. The electrode contacts 312, 314 may be interconnected with the electrodes 180, 182 of the stimulation component provided in the electronics package 310 in the body 302.

The distal electrode contact 314 may operate as a cathode for stimulation to the nerve 42. As discussed above, access to the nerve 42 may be minimized, such as with a small dissection relative to the nerve without full dissection of the nerve, to allow access of the distal electrode 314 to contact the nerve 42. The distal electrode 314 may be formed as a sphere or portion of a sphere to allow atraumatic insertion and remove of the electrode contact 314.

The body 302 may be positioned at any appropriate position relative to the patient 36, such as positions near the incision 45 that allows access to the nerve 42. Local soft tissue may be used to assist in holding the body portion 302 in place relative to the incision 45 during the procedure. According to various procedures, the body 302 may be positioned relative to the patient 36 following placement of the electrode 314 to contact (physically and/or electrically) the nerve 42.

The stimulation component 310 in the stimulation electrode 300 can then be operated to stimulate the nerve 42 during a selected procedure. The stimulation electrode 300, similar to the stimulation electrode 130 and the stimulation electrode 260, may not be directly connected to the monitor 20. Stimulation of the nerve 42 with the stimulation electronics 310 may be detected with the electrode 32 due to stimulation within the patient 36 and a selected signal received at the electrode 32 on the tube 38.

The contact electrode 314 may be connected to the body 302 and/or the electronics component 310 directly to the body 302 through a selected component, such as an elongated lead or proboscis 320. The contact electrode 314, therefore, may have a selected geometric shape such as generally or substantially spherical, cuboid, ovoid, etc. The selected geometric shape of the contact electrode 314 may, however, include a feature or surface contour (e.g. a flat, groove, etc.) to allow or assist in connecting the contact electrode 314 to the elongated lead 320.

The elongated lead 320 may include an electrically conductive connection, such as a metal wire. The proboscis 320 may include selected features such as being malleable, flexible, elastic, or the like. Accordingly, the contact electrode 314 may be positioned in contact with the nerve 42 and the proboscis 320 may be bent or flexed to a selected configuration to allow for efficient positioning of the body 302 relative to the patient 36 by the user 31. Further, the contact electrode 312 can be formed on the body 302 in any appropriate configuration or shape or location. For example, contact electrode 312 may form an entire surface of the body 302 other than being provided as a small patch that forms less than an entire surface of the body 302. Nevertheless, the provision of the two electrodes 312, 314 that may be positioned in direct contact with the patient 36 allows for monophasic or biphasic stimulation of the patient 36.

Moreover, the electronic components 310 may be formed to include the proboscis 320 and the contact electrode 314 extending therefrom. The body 302 may then be overmolded on the electronic component 310 in a single molding process. A mold formed to mold the body 302 onto the electronic component 310 may include the contact electrode 312 such that molding the body 302 is substantially a single and final step in forming the stimulation electrode 300. The assembly of the stimulation electrode 300, therefore, may include provision of the contact electrode 312 with the electronic component 310 including the proboscis 320 and the contact electrode 314, and then a final molding step to form the stimulation electrode 300. It is understood that various finishing steps may follow the molding steps, such as sterilization or polishing of the body 302, but that the stimulation electrode 300 is substantially finished and ready for operation after molding.

Figure 9A:
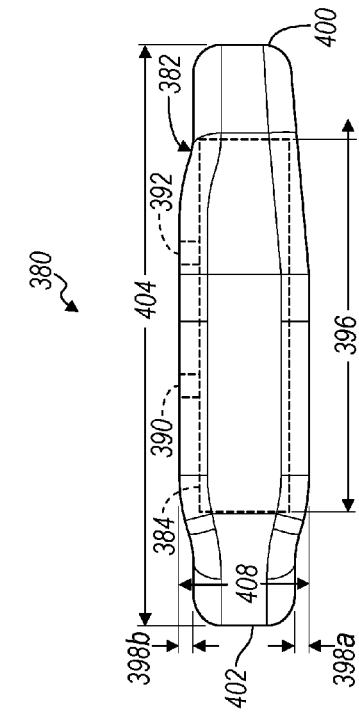
FIG. 9A is a perspective view of an electrode assembly, according to various embodiments.
Figure 9B:
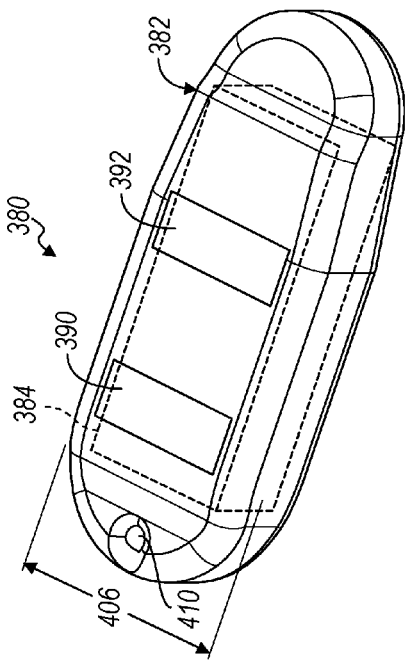
FIG. 9B is a side plan view of the electrode assembly of FIG. 9A.

Turning reference to FIGS. 9A and 9B, a stimulation electrode 380 is illustrated. The stimulation electrode 380 may be a leadless electrode assembly and includes a self-contained single unit electrode assembly having a housing 382 that is positioned (e.g. formed via molding) around an electronics package 384. As discussed above, the housing 382 may be formed around the electronics housing package 384 through various techniques such as an overmolding, including injection molding. The housing 382 may include passages or contact portions 390 and 392 that may form direct contact with the patient 36 for providing stimulation to the nerve 42. As discussed above, the contact 390, 392 may be included in the mold when overmolding the electronics package 384. Alternatively, the electrodes 180, 182 illustrated in FIG. 5A may extend above the printed circuit board 166 such that during the overmolding process a surface of the electrodes 180, 182 form the contact surfaces 390, 392 illustrated in FIG. 9A. Regardless, the stimulation electrode 380 may include two contacts 390, 392 for contacting and stimulating the patient 36.

The electronics package 384 may be substantially similar to or identical to the electronics assembly 160 illustrated in FIGS. 5A and 5B. The electronics package 384, therefore, may be operated to stimulate the patient as discussed above, in particular as discussed in relation to the flowchart 200.

The housing 382 may be formed to include a configuration to allow for ensured contact of the contacts 390, 392 with the nerve 42. For example, the housing 382 may include a raised region 396 that extends a distance 398 from an adjacent surface or region. The raised region 396 may extend from both sides or from two sides of the housing 382, as illustrated in FIG. 9B. The increased distance 398a, 398b may ensure a volume that is great enough to contact the nerve 42. Additionally, the tip or end regions 400 and 402 allow for a smaller cross-section for insertion of the stimulation electrode 380 relative to the nerve 42. Therefore, the stimulation electrode 380 may be inserted relative to the nerve 42 as a substantially single unit and at a single access point.

Further, the incision 45 of the patient 36 and dissection relative to the nerve 42 may be minimized by providing the stimulation electrode 380 as a single unit. Moreover, the dimensions of the single unit, for example the dimensions of the case 382 may include a length 404 that is about 10 millimeters (mm) to about 4 centimeters (cm) (about 40 mm). Further, a width 406 of the casing 382 may be about 5 mm to about 20 mm. A maximum height 408 of the case 382 may be about 2 mm to about 20 mm. Therefore, the volume of the casing 382 may be small and allow for ease of insertion into the patient 36. In various embodiments the stimulation electrode may have a maximum volume of about 16,000 cubic mm ($mm^3$).

Further, the casing 382 may include a passage 410. The passage 410 may allow for insertion of a suture or other grasping portion for easy removal of the stimulation electrode 380 from the patient 36. The stimulation electrode 380 may, therefore, be efficiently and without substantial or any trauma (e.g. atraumatically) be removed from the patient 36 following use. The suture may also serve as a reminder (i.e. a visual indicator) to the surgical staff of device presence to help minimize the possibility of becoming a retained surgical item. The suture of other handle may also be colored to provide a visual indication that the stimulation electrode is either present or not in the patient 36.

Turning reference to FIG. 10, a stimulation electrode 450 is illustrated. The stimulation electrode 450 may be a leadless electrode assembly and may include a body assembly 452 having a casing 454 that encloses an electronics package 456 which can be similar to the electronics assembly 160 discussed above. The PCB 166 can be formed to include or have connected thereto an extension or proboscis portion 460 that may be formed as a flexible circuit board or flex circuit. The flex circuit 460 may include traces to connect the PCB 166 with a first contact 462 and a second contact 464 at a terminal end 466 of the flexible PCB 460. The electrode contacts 462, 464 may be interconnected with the electrodes 180, 182, as discussed above. Further, it is understood that more than two electrode contacts 462, 464 may be provided on the proboscis 460. It would be further understood that an electrode contact may be provided on the casing 454, if selected.

According to various embodiments, the terminal end 466 may be positioned relative to the nerve 42 such that the nerve may pass over the contacts 462, 464. For example, as discussed above, an incision would be made relative to the nerve 42 and the terminal end 466 may be passed under a partially dissected nerve 42. Therefore, the two contacts 462, 464 may be provided to contact the nerve 42. In this manner, two contacts are provided to contact the nerve 42 directly for selected stimulation of the nerve 42. As discussed above, the stimulation of the nerve may be biphasic and may be altered over a selected period of time to ensure altering a type of stimulation of the nerve 42.

For example, as discussed above, the electrodes may selectively and individually operate as a cathode and an anode electrode. Therefore, during operation of the stimulation electrode 450, the controller 184 may include instructions to operate the contact 462 as an anode and the contact 464 as a cathode. After a selected period of time, the operation may be switched such that the contact 462 operates as the cathode and the contact 464 operates as the anode. In this manner, the contacts 462, 464 may be switched between cathode and anode over a set and/or predetermined period of time and for a set and/or predetermined period of time and may be off for a set and/or predetermined period of time between the switching.

According to various embodiments, the electrode 462 may be operated as the cathode and the electrode 464 may be operated as an anode for 100 milliseconds, both contacts may then be switched off for about 100 milliseconds, then the contact 462 may be operated as the anode and the contact 464 operated as the cathode for 100 milliseconds, and then both contacts may be switched off for a set period of time, such as about 500 milliseconds, and then the process repeated. Therefore, having the two contacts 462, 464 in direct contact with the nerve 42 may allow for operation of the stimulation electrode 450 in the manner of varying operation to attempt to ensure a selected stimulation of the nerve 42 during operation of the stimulation electrode 450.

The operation of the electrodes 462, 464 in a biphasic and/or switching manner may be based upon instructions saved in the memory 184b and executed with the processor 184a of the controller 184. Thus, the stimulation electrode may operate in an automatic manner once activated according to the instructions. The processor, in executing the instructions, may power the selected electrodes according to the predetermined operation as set out in the instructions saved on the memory 184b.

Turning reference to FIG. 11, a stimulation electrode 500 is illustrated. The stimulation electrode 500 may be a leadless electrode assembly and may be similar to the stimulation electrode 450 including a body 502 having a casing 454 that may house an electronics package 456. The electronics package 456 may be similar to the electronics assembly 160, as discussed above. Extending from the electronics package 456 may be an elongated member also referred to as a proboscis 520 and may be formed directly with the circuit board 166 or may be interconnected therewith. The proboscis 520 may be a flexible printed circuit and may include traces to contact or extend from the electrodes formed on the electronics package 506. The proboscis 520, however, may include a plurality of electrodes including a first electrode contact 522, a second electrode contact 524, a third electrode contact 526, and a fourth electrode contact 528.

During an operative procedure the proboscis 520 may be positioned such that all or a selected number of the contacts 520, 524, 526, and 528 contact the nerve 42, as illustrated in phantom FIG. 11. It is understood that all of the electrode contacts 522-528 need not directly contact the nerve 42. The controller 184 may determine, such as by executing instructions, which contacts are in contact with the nerve 42 based on resistance or load of the selected contacts when activated. Alternatively, the controller 184 may executes instructions to operate open loop in phased activation with operation commencing provided any two electrodes 522-528 are determined to be in contact with tissue, such as with a selected load or resistance.

As discussed above, the controller 184 may operate the plurality of contacts 462, 464 both in contact with the nerve 42 in a selected manner, such as switching the polarity of the contacts. Similarly, the plurality of contacts 522, 524, 526, and 528 may be operated in a similar alternating pattern to ensure a selected stimulation of the nerve 42. For example, two of the electrode contacts 522, 524 may be operated as anodes and two of the contacts 526, 528 may be operated as cathodes. It will be further understood that any number of the electrode contacts may be operated as cathodes or anodes for a selected period of time and may be switched to an alternate operation during a second period of time. Further, it will be understood that electrode contacts may be positioned both on the body 504 and on an opposite side of the proboscis 520 such that electrode contacts may be positioned at any appropriate location on the stimulation electrode 500.

Figure 12:
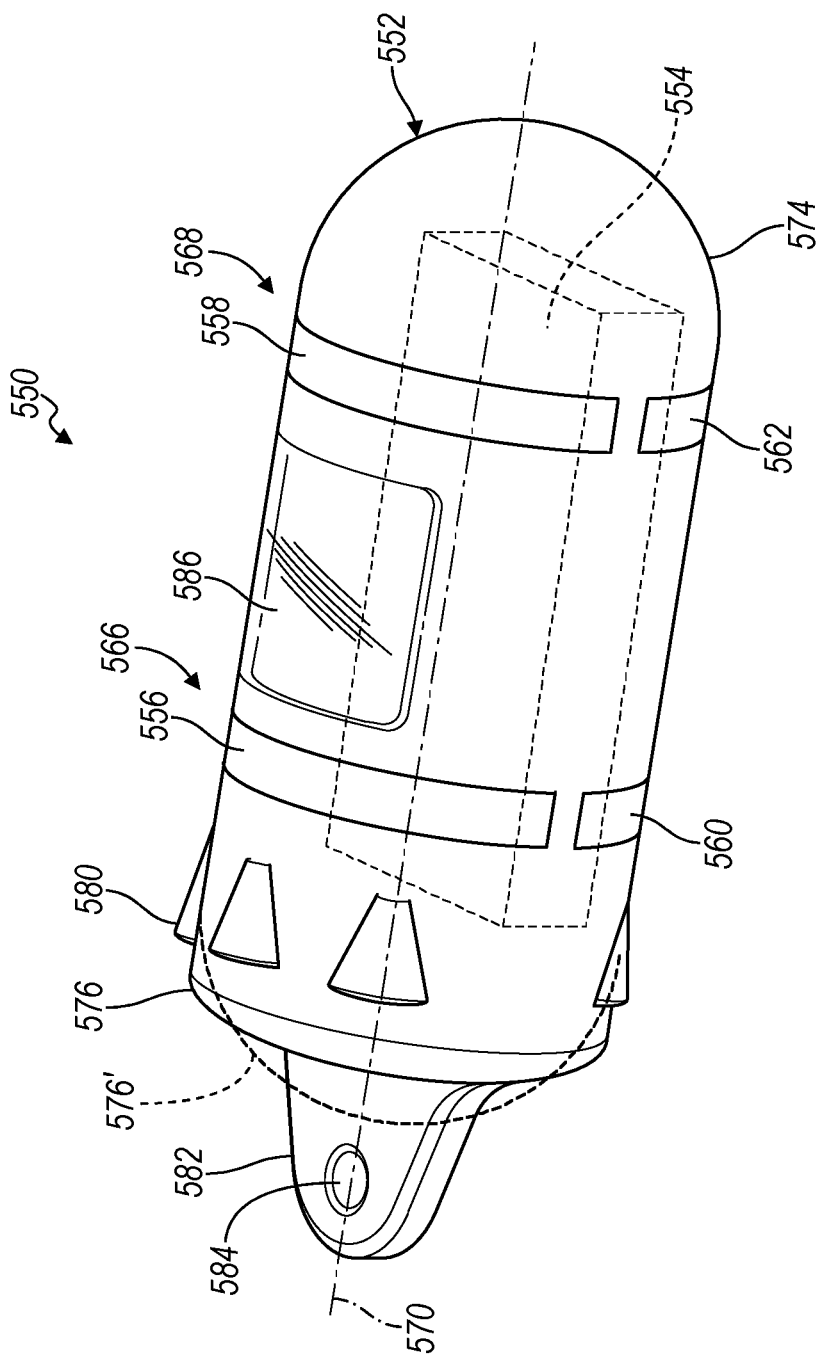
FIG. 12 is a perspective view of an electrode assembly, according to various embodiments.

A stimulation electrode 550, according to various embodiment, is illustrated in FIG. 12 and may include various portions and features similar to those discussed above. The stimulation electrode 550 may be a leadless stimulation electrode assembly, similar to the stimulation electrode 380 illustrated and discussed above. The simulation electrode 550 may include a body 552 that includes a housing for an electronics package 54 that may be similar or identical to the electronic assembly 160, as discussed above. The electronics package 554 may include various components, such as those discussed above, such as a controller, a memory, electrodes, a power source, and the like. The electronics package 554 may include electrodes or leads that extend to one or more electrodes or electrode contacts, including a first electrode contact 556 and a second electrode contact 558, a third electrode contact 560, and a fourth electrode contact 562. All of the electrode contacts 556-562 may be electrically or conductively connected to the electronics package 552.

Accordingly, the stimulation electrode 550 may include at least four electrodes 556, 558, 560, and 562. Each of the electrodes 556-562 may be electrically isolated from one another, such as with one or more breaks or discontinuities between conductive portions of the respective electrodes 556-562. The housing 552 may be formed of an insulating material, such as a selected non-conductive polymer or the like. The electrodes 556-562 can therefore be electrically isolated from one another by being separated by housing portions. It is further understood that more than four electrodes may be provided.

In various embodiments, the electrodes may be provided in a plurality of regions such as a first electrode region 566, which may include the first electrode 556 and the third electrode 560, and a second electrode region 568, including the second electrode 558 and the fourth electrode 562. It is understood, however, that more than two electrode regions 566 and 568 may be formed, such as formed axially along axis 570 of the stimulation electrode 550. For example, three or more of electrode regions may be formed along the axis 570 of the stimulation electrode 550.

Each electrode region may include more than two electrodes or contacts that are electrically separated from one another. For example, as illustrated in FIG. 12, the housing 552 may be substantially circular having a curved outer surface around the central axis 570. Therefore, each electrode or electrode contact may be formed in a quadrant and may be generally positioned about 90° from one another around the axis 570. Providing or having a number of electrodes smaller in size rather than fewer larger electrodes may minimize dissipation on the surface of the electrode relative to the tissue when providing stimulation to the subject 36. As discussed above, the stimulation electrode 550 may be positioned near the nerve 42 to provide stimulation at a selected rate, amplitude, or the like. Therefore providing electrodes at a selected position to stimulate the nerve 42 may make the stimulation more efficient and ensure a proper or selected lifetime of the stimulation electrode 550.

The stimulation electrode 550 having the housing 552 may include an appropriate shape and/or geometry, such as including a first curved end 574 and a second generally flat end 576. It is understood, however, that the second end may also be a curved end 576', shown in phantom. Therefore, the stimulation electrode 550 may be substantially symmetrical including first and second curved ends 574, 576'. However, a flat end 576 may be provided for various purposes, such as a selected geometry or length of the stimulation electrode 550. Further, one or more protrusions 580 may be formed to extend from an exterior surface of the housing 552. The protrusions 520 may be formed in a selected number and geometry to assist in resisting rolling of the stimulation electrode 550 on a surface, such as in an operating room, and fixation in tissue of subject 36. The protrusions 580 may assist in insertion and fixation of the stimulation electrode 550 in the subject 36 when positioned next to the nerve 42. The protructions 580 may be formed as barbs to allow ease of insertion, but resist withdrawal and/or rotation.

Further, the stimulation electrode 550 may include one or more tabs 582 that extend from the housing 552. The tab 582 may include a through bore 584 to engage or have passed therethrough a suture, as discussed above. The suture may be used to remove the stimulation electrode 550 from the subject 36 and/or provide indication to selected users that the stimulation electrode 550 is present.

Further, the housing 552 may include one or more transparent portions or windows 586. The transparent windows 586 may allow for access to an optical sensor, as discussed above and further herein. The optical sensor may be used to assist in activation or setting an inactivity of the stimulation electrode 550 for various purposes.

Each of the electrode or electrode sections 566 and 568 may extend substantially around the housing 552 of the stimulation electrode 550. By extending around the housing 552, the electrode sections 566 and 568 may allow for selected positioning of the stimulation electrode 550 within the subject 36. For example, in providing the electrode sections 566 and 568 to extend substantially around the housing 552, the stimulation electrode 550 may be substantially insensitive to rotation of the stimulation electrode 550 around the axis 570 once positioned with the subject 36. As each of the electrode sections 566 and 568 may have electrode or electrode contacts that operate for stimulation. Therefore, rotation of the stimulation electrode 550 around the axis 570 will not alter the contact of the electrodes in the electrode regions 566 and 568 relative to the selected portion of the patient 36, such as the nerve 42. Accordingly, as discussed above, with reference to the stimulation electrode 380, electrode or electrode contacts 390, 392 may be positioned on a selected surface, such as a single side, of a stimulation electrode 380. However, according to various embodiments, the stimulation electrodes may be provided as electrode regions or electrode portions 566, 568 as illustrated in the stimulation electrode 550. Each electrode portion or electrode contact of the electrode portions 566, 568 may be operated as stimulation electrodes. Thus, the stimulation electrode 550 may be less sensitive or substantially insensitive to movement, especially rotation, of the stimulation electrode 550 during or after positioning of the stimulation electrode 550 in the subject 36.

According to various embodiments, including those described above, stimulation electrode assemblies can be formed in a selected size such as including a body having a dimension similar to the body of the stimulation electrode 380, discussed above. Having a proboscis to extend from a body of selected embodiments may offer a plurality of options to position the electrode contacts at appropriate or selected positions relative to the nerve 42 of the patient 36. However, the stimulation electrodes may be provided at a selected volume to allow for ease and efficient positioning of the stimulation electrodes during an operative procedure.

As discussed above, the controller 184 may include the memory 184b that may include instructions that can be executed by the processor 184a. The instructions stored on the memory 184b can include instructions to operate the electrodes 180, 182 (or any appropriate number of electrodes) as discussed above. Therefore, the instructions may operate the electrodes in a constant polarity, switching polarity, and a pulsed manner, in a constant current and voltage manner and other appropriate manners. Therefore, once activated, the stimulator may operate according to the instructions stored in the memory 184b.

The instructions stored in the memory 184b may be executed substantially automatically upon activation of the controller 184. Thus, the leadless electrode assembly may be operated in a substantially autonomous manner. The instructions may be stored in the memory and the leadless electrode may be controlled by the processor 184a executing the instructions upon activation of the electrodes assembly 160. Accordingly, the leadless electrode assembly, according to various embodiments, may operate by executing instructions stored in the memory 184b included with the leadless electrode assembly.

The leadless electrode, according to various embodiments including those discussed above with the electronics assembly 160, therefore, may operate substantially autonomously and/or automatically to provide stimulation pulses once activated. The autonomous operation may be without any additional outside or external control of the stimulation pulses, timing, etc. For example, the monitor 20 or other parts of the system 16 may provide no control of the leadless electrode assembly. As discussed above, the leadless electrode may be activated to provide the stimulation pulses with no further control following activation by the user 31. Further, the activation component 190 may be the only user interaction with the leadless electrode other than placing and removing the leadless electrode. The stimulation signal from the pulses may be determined and/or displayed with the monitor 20.

Further, the instructions may be firmware instructions that may not be changed by the user 31. The instructions, however, may also be selectable instructions or programmable instructions that may be changed or stored to the memory 184b by the user 31 using various techniques, such as wireless transmission programming, hardware programming, or the like. Accordingly, transmission of the instructions to the memory 184b may be provided by the user 31. A firmware or non-volatile memory may be provided as the only memory of any stimulation electrode assembly, including various embodiments.

According to various embodiments, however, the stimulation electrodes, including the embodiments discussed above, are provided as a single use and ready-to-use system. Accordingly, during a selected procedure, the user 31 may open a package including the stimulation electrode, cause the stimulation electrode to be activated, and then place the stimulation electrode for the selected procedure. After completing the procedure, the stimulation electrode may be removed and discarded in an appropriate manner. Therefore, it may be selected to include the stimulation electrode as a substantially single use and ready-to-use system that may be positioned by the user 31 during a procedure.

The stimulation electrodes, as discussed above, including the stimulation components that are not directly connected to the monitor 20, may be operated and/or activated in various manners. According to various embodiments, to activate the stimulation electrode, the activation component 190 may be operated to activate the stimulation electrode. As discussed above, once activated the stimulation electrode may operate in a predetermined manner, such as based on the instructions stored in the memory 184b of the controller 184.

Activation of the stimulation electrode, including the electronics assembly 160, may be accomplished according to various manners. For example, the stimulation electrode may include the optical sensor 190 which may act as a switch upon sensing light through the transparent portion of the housing.

In one manner, the electronics assembly 160 may be activated once the optical component 190 is exposed to visible light. Accordingly, the stimulation electrode may be placed in opaque packaging that does not allow a substantial transmission of light to the optical component 190. Once the packaging is removed, the optical component may be exposed to visible light, such as in an operating theater, and this activates the electronics assembly 160. Similarly, during a prepackaging phase, the optical sensor 190 may be used to de-activate the electronics assembly 160. For example, the electronics assembly 160 may be tested in a manufacturing setting and the optical component 190 may be exposed to a selected frequency of light or blinking pattern to place the electronics assembly into inactive mode or arm it for subsequent single use 160. Therefore, the optical switch 190 may be used to activate and/or de-activate the electronics assembly 160.

Alternative or additional activation components may include a magnetic switch. For example, packaging for the stimulation electrode, according to various embodiments, may be incorporated into packaging for the stimulation component. Opening the packaging for the stimulation electrode may move a magnetic portion relative to the stimulation electrode which will activate the stimulation electrode. The stimulation electrode may also include a push switch or other physical switch that will activate the electronics assembly 160. Other physical switches may also include a pull tab that may be removed or engaged in the stimulation electrode to cause activation of the stimulation electrode.

Other activation components may include a loop that may be broken on the circuit board 166 that can cause activation of the electronics assembly 160 including powering the DC-to-DC convertor 212. A further physical switch may include a saline switch which may be included in the stimulation electrode. For example, a portion of foam may be wetted by a saline solution to cause a contact of a switch upon expansion of the foam portion due to wetting by a saline solution.

A further activation component may include a conductivity detection switch that may detect conductivity when the stimulation electrode assembly is positioned in the patient due to bodily fluids or contact with the nerve 42. Further, the conductivity switch may be activated by placing the stimulation electrode in contact with a saline or other conductive medium to cause activation of the stimulation electrode. Regardless of the activation component, however, evidence of activation may be provided to the user 31, such as with the LED indicator that the stimulation electrode is activated. Upon activation, the stimulation electrodes may be powered according to the controller 184 and, once positioned near the nerve, will stimulate the nerve 42 for monitoring with the monitoring system 20.

Example embodiments are provided so that this disclosure will be thorough, and will fully convey the scope to those who are skilled in the art. For example, activation portions, components, switches, and methods may be applied to the various electrode assemblies, as disclosed herein. The selected activation portions are not limited to any particular embodiments for any particular electrode assembly discussed herein. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A self-contained stimulation system, comprising:
   an electronics assembly having:
      a power source,
      an activation component,
      a controller having a memory and a processor, wherein the controller is configured to be activated by the activation component to set a signal, wherein the processor operates automatically to execute instructions stored on the memory to set the signal once activated with the activation component, and
      an electrode configured to deliver a current to a selected tissue based on the set signal; and
   a housing configured to contain at least the electronics assembly;
   a cuff member formed with the housing;
   an elongated member electrically connected to the electrode; and
   an electrode contact connected to the elongated member electrically connected to the electrode;
   wherein the housing is further configured, including size and shape, to be placed near a nerve to allow the electrode contact to contact a nerve.

2. The system of claim 1, further comprising:
   wherein the elongated member extends from the housing and electrically connected to the electrode.

3. The system of claim 2, wherein the electrode contact has a selected geometric shape at a terminal end of the elongated member.

4. The system of claim 2, wherein the elongated member is a flexible circuit;
   wherein the electrode contact is flat and formed on the flexible circuit.

5. The system of claim 4, wherein the electrode contact includes a plurality of electrode contacts;
   wherein each electrode contact of the plurality of electrode contacts is insulated from the each other electrode contact of the plurality of electrode contacts on the flexible circuit.

6. The system of claim 5, wherein the controller is further configured to execute the instructions to switch between powering and not powering each electrode of the plurality of electrodes individually.

7. The system of claim 1, further comprising:
   an electrode contact formed on the housing;
   wherein the electrode is configured to contact a nerve.

8. The system of claim 7, wherein the electrode contact extends around the housing to form a contact substantially 360° around an axis of the housing.

9. The system of claim 1, wherein the housing has a maximum volume of about 16,000 mm$^3$.

10. The system of claim 1, wherein the electronics assembly further includes an indicator configured to provide a visual signal of activation of the controller.

11. The system of claim 1, further comprising:
wherein the cuff member includes a first cuff portion moveable relative to a second cuff portion;
wherein the first cuff portion includes a first edge and the second cuff portion includes a second edge;
wherein the first edge and the second edge meet at plane that is defined at an angle of about plus 20 degrees to about minus 20 degrees relative to a surface of the housing.

12. The system of claim 11, further comprising:
a first electrode contact extending into an area at least partially enclosed by the cuff member.

13. A stimulation system, comprising:
a housing extending generally along a plane;
a cuff member formed with the housing;
an elongated member electrically connected to the electrode; and
an electrode contact connected to the elongated member electrically connected to the electrode;
wherein the housing is further configured, including size and shape, to be placed near a nerve to allow the electrode contact to contact a nerve;
wherein the cuff member includes a first cuff portion moveable relative to a second cuff portion;
wherein the first cuff portion includes a first edge and the second cuff portion includes a second edge;
wherein the first edge and the second edge meet in an opening region that is defined at an angle of about plus 5° to about plus 20° to about minus 5° to about minus 20° relative to the plane extending through the cuff member where the first edge and the second edge meet when the cuff member is closed.

14. The system of claim 13, further comprising:
a monitor configured to receive a signal;
an electrode contact within the cuff member and configured to be placed in contact with a nerve;
a driver to drive a signal;
a lead extending from the electrode contact to the driver to deliver the signal to the electrode contact and to the nerve.

15. The system of claim 13, wherein the first edge and the second edge are configured to have complimentary wave shapes to allow substantially complete contact along an entire length of the first edge and the second edge.

16. The system of claim 13, further comprising:
an electronics assembly having:
a power source,
an activation component,
a controller configured to be activated by the activation component to send a signal, and
an electrode configured to deliver a current to a selected tissue upon receiving the signal; and
wherein the housing configured to contain the electronics assembly.

17. The system of claim 16, further comprising:
a cuff lever arm connected to the first cuff portion to move the first cuff portion.

18. The system of claim 16, further comprising:
an electrode contact extending into an area at least partially enclosed by the cuff member;
wherein the electrode contact is configured to deliver a signal generated by the controller.

19. A method of providing a stimulator system, comprising:
forming an electronics assembly having: a power source, an activation component, a controller configured to be activated by the activation component to send a signal, and an electrode configured to deliver a current to a selected tissue upon receiving the signal; and
housing the electronics assembly within a housing portion, wherein the housing portion has a configuration for placement in a patient;
providing a cuff member formed with the housing, an elongated member electrically connected to the electrode, an electrode contact connected to the elongated member electrically connected to the electrode;
providing the housing to have a size and shape to be placed near a nerve to allow the electrode contact to contact the nerve.

20. The method of claim 19, wherein housing the electronics assembly within a housing portion includes overmolding at least a portion of the electronics assembly.

21. The method of claim 20, wherein the overmolding at least a portion of the electronics assembly includes maintaining at least a portion of the electrode exposed through the housing.

22. The method of claim 20, wherein the overmolding at least a portion of the electronics assembly includes providing an electrode contact within a mold to have electrical connection to the electrode after overmolding the electronics assembly.

23. The method of claim 19, further comprising:
placing the housing portion that is housing the electronics assembly near a nerve of a subject to stimulate the nerve.

24. The method of claim 19, further comprising:
activating the electronics assembly with the activation component.

25. The method of claim 24, further comprising:
operating the controller to send a stimulation signal to the electrode by the activating the electronics assembly.

26. The method of claim 24, wherein activating the electronics assembly includes at least one of exposing the activation component to light energy, exposing the activation component to a conductive medium, detecting a resistance at the electrode, operating a mechanical switch that forms the activation component, moving a magnet relative to the activation component, or combinations thereof.

27. The method of claim 19, further comprising:
placing an electrode contact that is in electrical connection with the electrode near a nerve of a subject to stimulate the nerve.

28. The method of claim 27, further comprising:
providing an electrode contact on an elongated member extending from the housing portion;
wherein the electrode contact is in electrical connection with the electrode.

* * * * *